United States Patent [19]
Pye et al.

[11] Patent Number: 6,130,334
[45] Date of Patent: Oct. 10, 2000

[54] PROCESS FOR MAKING 2-ARYL-3-ARYL-5-HALO PYRIDINES USEFUL AS COX-2 INHIBITORS

[75] Inventors: Philip J. Pye, Guttenberg; Ashok Maliakal, Rahway; Kai Rossen, Westfield; Ralph P. Volante, Cranbury; Jess Sager, Bridgewater, all of N.J.

[73] Assignee: Merck & Co., Inc., Rahway, N.J.

[21] Appl. No.: 09/060,731

[22] Filed: Apr. 15, 1998

[51] Int. Cl.[7] .................... C07C 255/34; C07C 255/43; C07C 317/14; C07D 213/84; C07D 213/46

[52] U.S. Cl. .................... 546/286; 546/257; 546/287; 546/298; 546/300; 546/315; 558/413; 568/29; 568/30; 568/31; 568/33

[58] Field of Search ...................... 546/298, 300, 546/315, 286, 287, 314; 558/413; 568/29, 30, 31, 33

[56] References Cited

U.S. PATENT DOCUMENTS

| | | |
|---|---|---|
| 5,474,995 | 12/1995 | Ducharme et al. .............. 514/241 |
| 5,677,318 | 10/1997 | Lau ................................. 514/361 |

FOREIGN PATENT DOCUMENTS

| | | |
|---|---|---|
| 2 221 546 | 5/1972 | Germany . |
| 22 21 546 | 5/1972 | Germany . |
| 561 202 | 5/1971 | Switzerland . |
| WO 96/24584 | 8/1996 | WIPO . |
| WO 96/25405 | 8/1996 | WIPO . |
| WO 96/38442 | 12/1996 | WIPO . |
| WO 98/03484 | 1/1998 | WIPO . |

*Primary Examiner*—Alan L. Rotman
*Attorney, Agent, or Firm*—Raynard Yuro; Richard C. Billups; David L. Rose

[57] ABSTRACT

The invention encompasses a process for making compounds of Formula I useful in the treatment of cyclooxygenase-2 mediated diseases.

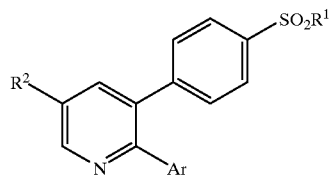

2 Claims, No Drawings

PROCESS FOR MAKING 2-ARYL-3-ARYL-5-HALO PYRIDINES USEFUL AS COX-2 INHIBITORS

CROSS REFERENCE TO RELATED APPLICATIONS

This application claims the benefit of U.S. Provisional application No. 60/045,642, filed on April 18, 1997.

BACKGROUND OF THE INVENTION

This invention concerns a process for making certain anti-inflammatory compounds. In particular, the application concerns a process for making compounds of formula I as disclosed hereinunder, which compounds are potent cyclooxygenase-2 inhibitors.

Non-steroidal, antiinflammatory drugs exert most of their antiinflammatory, analgesic and antipyretic activity and inhibit hormone-induced uterine contractions and certain types of cancer growth through inhibition of prostaglandin G/H synthase, also known as cyclooxygenase. Up until recently, only one form of cyclooxygenase had been characterized, this corresponding to cyclooxygenase-1 or the constitutive enzyme, as originally identified in bovine seminal vesicles. Recently the gene for a second inducible form of cyclooxygenase (cyclooxygenase-2) has been cloned, sequenced and characterized from chicken, murine and human sources. This enzyme is distinct from the cyclooxygenase-1 which has now also been cloned, sequenced and characterized from sheep, murine and human sources. The second form of cyclooxygenase, cyclooxygenase-2, is rapidly and readily inducible by a number of agents including mitogens, endotoxin, hormones, cytokines and growth factors. As prostaglandins have both physiological and pathological roles, we have concluded that the constitutive enzyme, cyclooxygenase-1, is responsible, in large part, for endogenous basal release of prostaglandins and hence is important in their physiological functions such as the maintenance of gastrointestinal integrity and renal blood flow. In contrast, we have concluded that the inducible form, cyclooxygenase-2, is mainly responsible for the pathological effects of prostaglandins where rapid induction of the enzyme would occur in response to such agents as inflammatory agents, hormones, growth factors, and cytokines. Thus, a selective inhibitor of cyclooxygenase-2 will have similar antiinflammatory, antipyretic and analgesic properties to a conventional non-steroidal antiinflammatory drug, and in addition would inhibit hormone-induced uterine contractions and have potential anti-cancer effects, but will have a diminished ability to induce some of the mechanism-based side effects. In particular, such a compound should have a reduced potential for gastrointestinal toxicity, a reduced potential for renal side effects, a reduced effect on bleeding times and possibly a lessened ability to induce asthma attacks in aspirin-sensitive asthmatic subjects.

WO 96/24585 published Aug. 15, 1996 and WO 96/10012, published Apr. 4, 1996 disclose methods of making 2-aryl-3-aryl-pyridines. In the invention as descloses hereinunder, 2-aryl-3-aryl-pyridines are prepared in a simple to conduct, 1 step condensation from readily available starting materials. It is, therefore, surprisingly convenient and more efficient than the prevoiusly described procedure, in which the 2-aryl-3-aryl pyridine was constructed by serial stepwise addition of the aryl groups to the central pyridine ring. Moreover, the the process of the instant invention is also surprisingly superior in that expensive palladium reagents are not required nor is the combersome protection/de-protection sequense of the prior art process.

The preparation of 2-chloromalondialdehyde was first accomplished by Diekmann in 1904 (W. Dieckmann, L. Platz, Ber. Deut. Chem. Ges. 1904, 37, 4638). The chemistry of 2-halomalondialdehydes was thoroughly reviewed in 1975 (C. Reichardt and K. Halbritter, Angew. Chem. Int. Ed. 1975, 14, 86). This review does not mention a pyridine synthesis using these reagents. The only recorded use of 2-chloromalondialdehyde for the preparation of a pyridine is in a recent patent application (F. J. Urban, U.S. Pat. No. 5,206,367 to Pfizer and Brackeen, M. and Howard, H. R. European Patent Application number 89307339.5 (EP 0 352 959) to Pfizer), where chloromalondialdehyde is first converted to 2,3-dichloroacrolein, which is subsequently condensed with the enamine derived from 1,3-cyclohexanedione to give the annulated pyridine in 28% yield.

A recent comprehensive review of pyridine synthesis and reactivity (D. Spitzner in Methoden der Organischen Chemie (Houben-Weyl), pages 286 to 686, Vol. E 7b, Editor R. P. Kreher, 1992, Georg Thieme Verlag) gives no examples for the use of halomalondialdehydes for the pyridine synthesis. Nitromalondialdehyde has been condensed with ethyl-2-amino-crotonate to give the 5-nitropyridine, albeit in lower yield (35–50%) (J. M. Hoffman et.al. J. Org. Chem. 1984, 49, 193 and P. E. Fanta, J. Am. Chem. Soc. 1953, 75, 737). The use of ethoxycarbonyl malondialdehyde derivatives leads to 5-ethoxycarbonyl pyridines (S. Torii et. al. Synthesis, 1986, 400).

SUMMARY OF THE INVENTION

The invention encompasses a process for making compounds of Formula I useful in the treatment of inflammation and other cyclooxygenase-2 mediated diseases

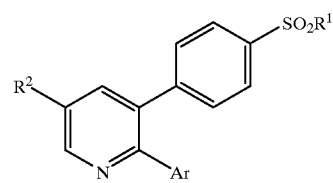

I

DETAILED DESCRIPTION OF THE INVENTION

In a first aspect the invention encompasses a process for making compounds of Formula I useful in the treatment of inflammation and other cyclooxygenase-2 mediated diseases

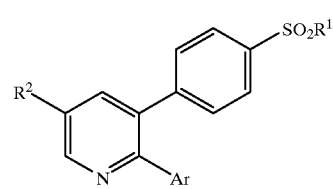

I wherein:
$R^1$ is selected from the group consisting of
(a) $CH_3$,
(b) $NH_2$, (c) NHC(O)CF$_3$,
(d) NHCH$_3$;

Ar is a mono-, di-, or trisubstituted phenyl or pyridinyl (or the N-oxide thereof), wherein the substituents are chosen from the group consisting of
(a) hydrogen,
(b) halo,
(c) C$_{1-4}$alkoxy,
(d) C$_{1-4}$alkylthio,
(e) CN,
(f) C$_{1-4}$alkyl,
(g) C$_{1-4}$fluoroalkyl, R$^2$ is chosen from the group consisting of
(a) F, Cl, Br, I
(b) CN,
(c) azide, the process comprising:
condensing a compound of formula A1

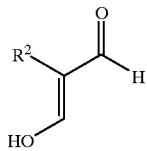

A1 under acidic conditions, and optionally in the presence of a non-reactive solvent and in the presence of an ammonium reagent, with compound A2

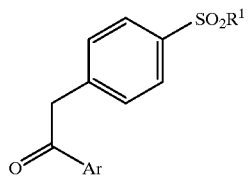

A2 to yield a compound of Formula I

As will be appreciated by those of skill in the art, in the general case the reagents themselves provide the acidic condition.

Therfore, the use of a non-reagent acid is not necessary. However, the addition of an acid, such as acetic or propionic or another carboxylic acid is within the scope of the invention.

For purposes of this specification non-reactive solvent includes tetrahydrofuran, dioxane, C$_{1-6}$alkanol, and toluene.

For purposes of this specification, the ammonium reagent is intended to include ammonia and ammonim salts such as ammonium acetate and ammonium propionate. Moreover a mixture ammonia reagent species is included in the term ammonia reagent.

The molar ratio of compound A1 to A2 can typically be varied from 2:1 to 1:2; preferably 1:1 to 1.5. Excess compound A1 is typically used. The molar ratio of compound A1 to ammonium reagent can typically be varied from 1:1 to 1:10. The reaction step may conveniently be conducted at a temperature range of 40 to 180° C.; preferably 80 to 140° C. and is allowed to proceed until substantially complete in from 2 to 18 hours; typically 6 to 12 hours.

In a second aspect the invention encompasses a process for making compounds of Formula I useful in the treatment of inflammation and other cyclooxygenase-2 mediated diseases

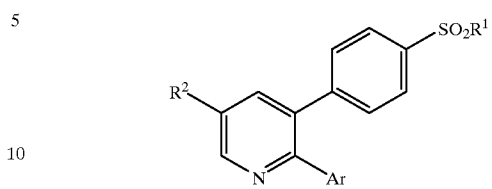

I wherein:
R$^1$ is selected from the group consisting of
(a) CH$_3$,
(b) NH$_2$,
(c) NHC(O)CF$_3$,
(d) NHCH$_3$;

Ar is a mono-, di-, or trisubstituted phenyl or pyridinyl (or the N-oxide thereof), wherein the substituents are chosen from the group consisting of
(a) hydrogen,
(b) halo,
(c) C$_{1-4}$alkoxy,
(d) C$_{1-4}$alkylthio,
(e) CN,
(f) C$_{1-4}$alkyl,
(g) C$_{1-4}$fluoroalkyl, R$^2$ is chosen from the group consisting of
(a) F, Cl, Br, I
(b) CN,
(c) azide, the process comprising:
(a) reacting a compound of formula A2

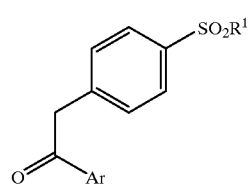

A2 in the presence of a second non-reactive solvent with a strong base to yield the enolate of formula B1

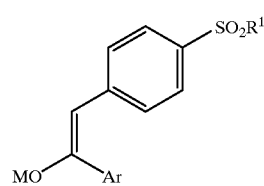

B1 wherein M is potassium, lithium or sodium.

For purposes of this specification, the strong base shall include lithium, potassium or sodium diisopropylamide, lithium, potassium or sodium bis(trimethylsilyl)amide, lithium, potassium or sodium hydride, and lithium, potassium or sodium amide.

For purposes of this specification the second non-reactive solvent includes tetrahydrofuran, dioxane, toleune and ethers.

The molar ratio of compound A2 to base can typically be varied from 1:1 to 1:1.5. Excess base is typically used. The reaction step may conveniently be conducted at a temperature range of −80 to 40° C.; preferably −10 to 20° C. and is allowed to proceed until substantially complete in from 1 to 3 hours; typically 1 to 2 hours.

(b) reacting a compound of formula B1

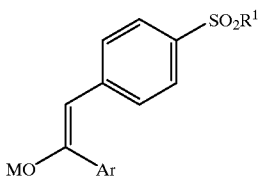

B1 in the presence of a third non-reactive solvent with compound B2

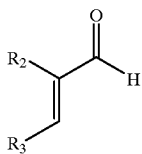

B2 wherein $R^3$ is a leaving group such as tosyl, mesyl or halo. which after heating in the presence of ammonia reagent, yields a compound of formula I.

For purposes of this reaction, the third non-reactive solvent shall include tetrohydrofuran, toluene and dioxane. The molar ratio of compound B1 to 2.3-dichloroacrolein can typically be varied from 1:1.5 to 1.5:1; preferably 1:1 to 1.5. Excess 2.3-dichloroacrolein is typically used. The reaction step may conveniently be conducted at a temperature range of 0 to 80° C.; preferably 20 to 50° C. and is allowed to proceed until substantially complete in from 2 to 18 hours; typically 4 to 12 hours.

With regard to the both aspects of the invention, $R^2$ is preferably halogen, most preferably F or Cl, most preferably Cl. It is preferable that 113 be the same as $R^2$.

With regard to both aspects of the invention a preferred sub-genus of formula I is that wherein Ar is a mono-, or disubstituted pyridinyl. Within this sub-genus, the 3-pyridinyl isomers are particularly preferred.

Again with regard to both aspects of the invention another preferred sub-genus of formula I is that wherein $R^1$ is $CH_3$ or $NH_2$. Generally, $CH_3$ is preferred for COX-2 specificity and $NH_2$ is preferred for potency.

Again with regard to both aspects of the invention another preferred sub-genus of formula I is that wherein the Ar is unsubstituted or substituted with $CH_3$.

The Compound of Formula I is useful for the relief of pain, fever and inflammation of a variety of conditions including rheumatic fever, symptoms associated with influenza or other viral infections, common cold, low back and neck pain, dysmenorrhea, headache, toothache, sprains and strains, myositis, neuralgia, synovitis, arthritis, including rheumatoid arthritis degenerative joint diseases (osteoarthritis), gout and ankylosing spondylitis, bursitis, burns, injuries, following surgical and dental procedures. In addition, such a compound may inhibit cellular neoplastic transformations and metastic tumor growth and hence can be used in the treatment of cancer. Compounds of formula I may also be useful for the treatment of dementia including pre-senile and senile dementia, and in particular, dementia associated with Alzheimer Disease (i.e. Alzheimer's dementia).

By virtue of its high cyclooxygenase-2 (COX-2) activity and/or its selectivity for cyclooxygenase-2 over cyclooxygenase-1 (COX-1) as defined above, compounds of formula I will prove useful as an alternative to conventional non-steroidal antiinflammatory drugs (NSAID'S) particularly where such non-steroidal antiinflammatory drugs may be contra-indicated such as in patients with peptic ulcers, gastritis, regional enteritis, ulcerative colitis, diverticulitis or with a recurrent history of gastrointestinal lesions; GI bleeding, coagulation disorders including anemia such as hypoprothrombinemia, haemophilia or other bleeding problems (including those relating to reduced or impaired platelet function); kidney disease (e.g. impaired renal function); those prior to surgery or taking anticoagulants; and those susceptable to NSAID induced asthma.

Compounds of the present invention are inhibitors of cyclooxygenase-2 and are thereby useful in the treatment of cyclooxygenase-2 mediated diseases as enumerated above. This activity is illustrated by their ability to selectively inhibit cyclooxygenase-2 over cyclooxygenase-1. Accordingly, in one assay, the ability of the compounds of this invention to treat cyclooxygenase mediated diseases can be demonstrated by measuring the amount of prostaglandin $E_2$ ($PGE_2$) synthesized in the presence of arachidonic acid, cyclooxygenase-1 or cyclooxygenase-2 and a compound of formula I. The IC50 values represent the concentration of inhibitor required to return $PGE_2$ synthesis to 50% of that obtained as compared to the uninhibited control. Illustrating this aspect, we have found that the Compounds of the Examples are more than 100 times more effective in inhibiting COX-2 than they are at inhibiting COX-1. In addition they all have a COX-2 IC50 of 1 nM to 1 mM. By way of comparison, Ibuprofen has an IC50 for COX-2 of 1 mM, and Indomethacin has an IC50 for COX-2 of approximately 100 nM.

For the treatment of any of these cyclooxygenase mediated diseases, compounds of formula I may be administered orally, topically, parenterally, by inhalation spray or rectally in dosage unit formulations containing conventional non-toxic pharmaceutically acceptable carriers, adjuvants and vehicles. The term parenteral as used herein includes subcutaneous injections, intravenous, intramuscular, intrasternal injection or infusion techniques. In addition to the treatment of warm-blooded animals such as mice, rats, horses, cattle sheep, dogs, cats, etc., the compound of the invention is effective in the treatment of humans.

The invention will now be illustrated by the following non-limiting examples in which, unless stated otherwise:
(i) all operations were carried out at room or ambient temperature, that is, at a temperature in the range 18–25° C.; evaporation of solvent was carried out using a rotary evaporator under reduced pressure (600–4000 pascals: 4.5–30 mm. Hg) with a bath temperature of up to 600° C.; the course of reactions was followed by thin layer chromatography (TLC) or High Pressure Liquid Chromatography (HPLC) and reaction times are given for illustration only; melting points are uncorrected and 'd' indicates decomposition; the melting points given are those obtained for the materials prepared as described; polymorphism may result in isolation of materials with different melting points in some preparations; the structure and purity of all final products were assured by at least one of the following techniques: TLC, mass spectrometry, nuclear magnetic resonance (NMR) spectrometry or microanalytical data; yields are given for illustration only; when given, NMR data is in the form of delta (d) values for major diagnostic protons, given in parts per million (ppm) relative to tetramethylsilane (TMS) as internal standard, determined at 300 MHz or 400 MHz using the indicated solvent; conventional abbreviations used for signal shape are: s. singlet; d. doublet; t. triplet; m. multiplet; br. broad; etc.: in addition "Ar" signifies an aromatic signal; chemical symbols have their usual meanings; the following abbreviations have also been used v (volume), w (weight), b.p. (boiling point), m.p. (melting point), L (liter(s)), mL (milliliters), g (gram(s)), mg (milligrams(s)), mol (moles), mmol (millimoles), eq (equivalent(s)).

The following abbreviations have the indicated meanings:

Alkyl Group Abbreviations

- Me=methyl
- Et=ethyl
- n-Pr=normal propyl
- i-Pr=isopropyl
- n-Bu=normal butyl
- i-Bu=isobutyl
- s-Bu=secondary butyl
- t-Bu=tertiary butyl
- c-Pr=cyclopropyl
- c-Bu=cyclobutyl
- c-Pen=cyclopentyl
- c-Hex=cyclohexyl

EXAMPLE 1

5-Chloro-3(methylsulfonyl)phenyl-2-(3-pyridyl)-pyridine; Compound 1

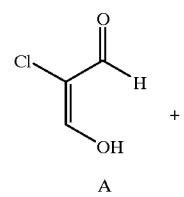

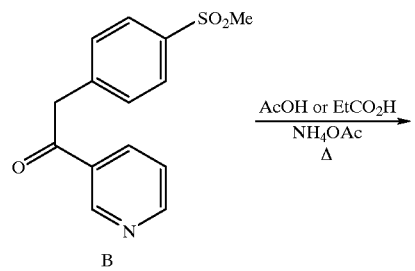

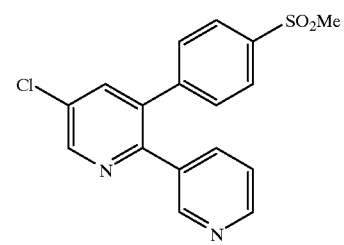

| 2-Chloromalondialdehyde | 4.8 g (0.045 mol) |
| --- | --- |
| Ketone B | 5.0 g (0.018 mol) |
| Propionic acid | 30 mL |
| Ammonium Acetate | 8.4 g (0.11 mol) |

A mixture of ketone B (5.0 g), 2-chloromalondialdehyde (4.8 g) and ammonium acetate were heated to 130° C. The acetic acid produced was removed by distillation and heating continued at 136° C. for 15 hours. The reaction mixture was basified with sodium carbonate, water was added and the product was extracted into dichloromethane (2×150 mL). The organic layers were carbon treated (Dowex), dried (MgSO$_4$) and the solvent removed to afford 1 as an off white solid (3.4 g, 55% yield).

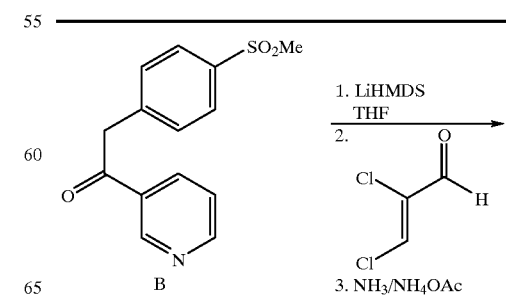

| 2-Choromalondialdehyde | 220 mg (2.1 mmol) |
| --- | --- |
| Oxalyl Chloride | 180 mL (2.1 mmol) |
| Toluene | 3 mL |
| N,N-Dimethylformamide | 20 mL |

N,N-dimethyl formamide was added to a slurry of 2-chloromalondialdehyde (220 mg) in toluene. Oxalyl chloride was added and the reaction mixture was stirred until complete dissolution occurred.

-continued

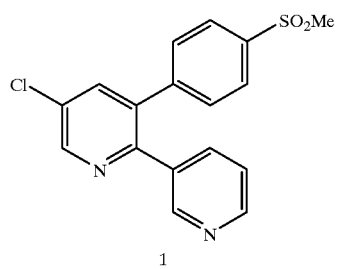

| Ketone B | 500 mg (1.8 mmol) |
| Lithium bis(trimethylsilyl)amide (1M in THF) | 1.8 mL (1.8 mmol) |
| Tetrahydrofuran | 15 mL |
| 2,3-Dichloroacrolein in toluene | 2.1 mmol in 3 mL toluene |
| Ammonium acetate | 1.0 g |

Lithium bis(trimethylsilyl)amide (1.8 mL;1 M in THf) was added dropwise to ketone B (500 mg) in THF (15 mL) at −78° C. The reaction mixture was warmed to ambient temperature for 1 hour to form the lithium enolate of B (see the generic formula B1) before recooling to 78° C. A solution of 2,3-dichloroacrolein was added and the temperature allowed to warm to room temperature. After 1 hour ammonia gas was passed through the solution and after 30 minutes ammonium acetate (1 g) was added. The reaction mixture was warmed to 60° C. for 1 hour and poured into aqueous sodium hydroxide (2 M; 100 mL). The product was extracted with dichloromethane (2×150 mL), dried (MgSO4) and the solvent removed to afford 1 (500 mg; 80%).

PREPARATION OF STARTING MATERIALS

PREP 1

SYNTHESIS OF 4-METHYLSULFONYLPHENYLACETIC ACID

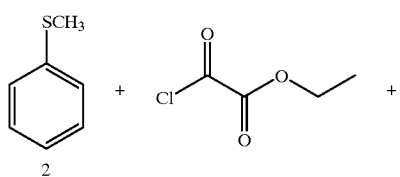

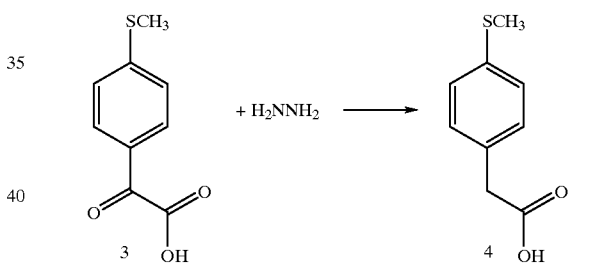

| Thioanisole 2 (FW = 124.2, d = 1.058) | 50.00 g (0.403 mol, 47.3 mL) |
| Ethyloxalyl chloride (FW = 136.5, d = 1.222) | 82.43 g (0.604 mol, 67.5 mL) |
| Aluminum chloride (FW = 133.3) | 75.13 g (0.564 mol) |
| o-dichlorobenzene (ODCB) | 112 mL |

The ethyloxalyl chloride and ODCB were charged to a flask equipped with an overhead mechanical stirrer and cooled to 0° C. The AlCl$_3$ was added slowly. The addition of the AlCl$_3$ was exothermic. The thioanisole 2 was added dropwise via an addition funnel over 1.5 h. The reaction mixture rapidly turns a dark violet color. This addition was also exothermic.

After 1 h, the reaction was complete by HPLC. The reaction was quenched by the slow addition of 300 mL of 1N HCl at 0° C. After warming to room temperature, water and ODCB (50 mL each) were added. The layers were mixed and cut. The organic (bottom) phase was washed with 1×250 mL water and then dried over MgSO$_4$.

This quench was also exothermic. The reaction mixture turned from dark violet to pale green during the quench. The dried ODCB solution was charged to a Morton flask equipped with mechanical stirring. A solution of 1N NaOH (800 mL) was added. The biphasic mixture was stirred vigorously and heated to 50° C. Hydrolysis to 3 was complete in 2–3 h by HPLC. The product-containing aqueous phase was taken directly into the Wolf-Kishner reaction.

4-tethalthio)phenylacetic acid

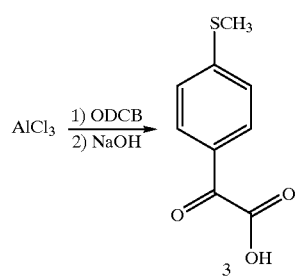

| 3 (in 1N NaOH solution) | (0.402 mol) |
| Hydrazine (FW = 32.1, 35 wt % in water) | 206.14 g (2252 mol, 204 mL) |
| NaOH (5N solution) | 5 mL |

The hydrazine and NaOH were charged to a Morton flask equipped with mechanical stirring. After heating the hydrazine solution to 75° C., the solution of 3 in NaOH was added over 35–40 min. At the end of the addition the reaction mixture was brought to reflux for 5 days. HPLC showed the reaction to be ca. 95% complete at this point. The starting material was largely consumed in under 24 h, but a third peak which took several days to convert to 4. The reaction was acidified with concentrated HCl to pH=1.5 and extracted with EtOAc (1×750 mL and 1×250 mL). The combined product-containing organic phases were washed 2×250 mL 1N HCl.

On acidification, the reaction mixture turned bright yellow.

4-(Methanesulfonyl)phenylacetic acid

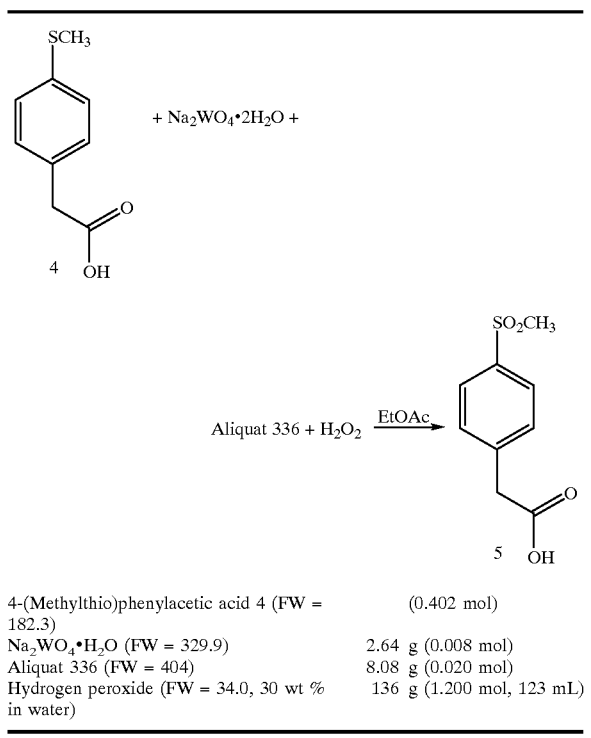

| | |
|---|---|
| 4-(Methylthio)phenylacetic acid 4 (FW = 182.3) | (0.402 mol) |
| Na$_2$WO$_4$·H$_2$O (FW = 329.9) | 2.64 g (0.008 mol) |
| Aliquat 336 (FW = 404) | 8.08 g (0.020 mol) |
| Hydrogen peroxide (FW = 34.0, 30 wt % in water) | 136 g (1.200 mol, 123 mL) |

A flask equipped for mechanical stirring was charged with 3 (from reaction above, in EtOAc), Aliquat 336, and Na$_2$WO$_4$·2H$_2$O (dissolved in ca. 15 mL H$_2$O). Hydrogen peroxide was added slowly via an addition funnel over ca. 30 min. Completion of reaction was checked by HPLC. The reaction was washed with 2×400 mL H$_2$O and dried over MgSO$_4$. Quantification of product in the organic layer gave 61.29 g 5 (71% yield from thioanisole). On concentration of the solution, a white solid precipitated. The slurry was filtered, and washed with hexanes. Recovery was 49.02 g 5 (57% from thioanisole).

Ivanov-Claisen Condensation for the Preparation of 1-(3-pyridyl)-2-(4-methylsulfonylphenyl)-ethane-1-one

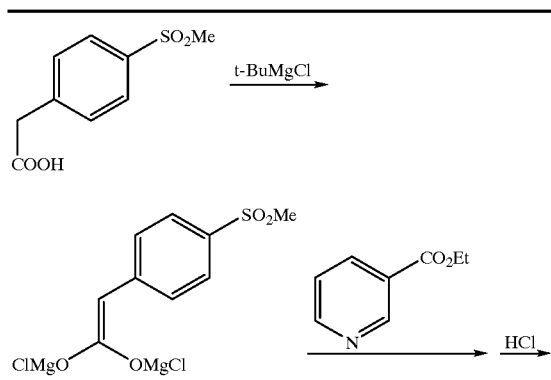

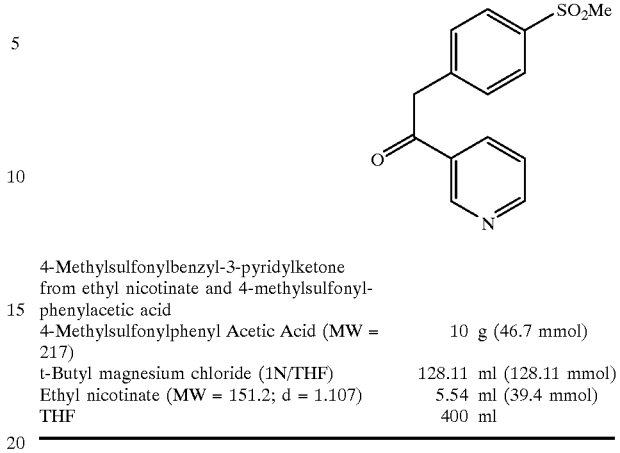

4-Methylsulfonylbenzyl-3-pyridylketone from ethyl nicotinate and 4-methylsulfonyl-phenylacetic acid

| | |
|---|---|
| 4-Methylsulfonylphenyl Acetic Acid (MW = 217) | 10 g (46.7 mmol) |
| t-Butyl magnesium chloride (1N/THF) | 128.11 ml (128.11 mmol) |
| Ethyl nicotinate (MW = 151.2; d = 1.107) | 5.54 ml (39.4 mmol) |
| THF | 400 ml |

Phenyl acetic acid was dissolved in THF under nitrogen. 1.9 equivalents (88.73 ml) of t-butyl magnesium chloride were added over 5 minutes to the solution. The Reaction was exothermic. The temperature rose from 20° C. to 50° C. After addition of the first equivalent of t-butyl magnesium chloride, the solution turned red.

The reaction temperature was maintained at 50° C. After one hour, 0.5 equivalents of ethyl nicotinate were added. The solution turned yellow and a white precipitate formed. After one hour, 0.5 equivalents of t-butyl magnesium chloride were added at 50° C. The solution turned red. This sequence of addition was repeated using 0.25 eq., 0.125 eq., 0.0625 eq. of ethyl nicotinate and t-butyl magnesium chloride. The reaction mixture was aged for 1 hour between each addition.

After the last addition, the reaction was quenched by adding the reaction mixture into vigorously stirred 2N hydrochloric acid (100 ml). The solids at the bottom of the reaction mixture dissolved with effervescence when stirred in hydrochloric acid.

The pH of the aqueous phase of the reaction mixture was adjusted to 10 with sodium carbonate. LC assay showed 91% yield of ketone Preparation of 4-Methylsulfonylbenzaldehyde The preparation follows the procedure of Ulman JOC, pp4691 (1989).

4-Methylsulfonylbenzaldehyde (2) from 4-Fluorobenzaldehyde

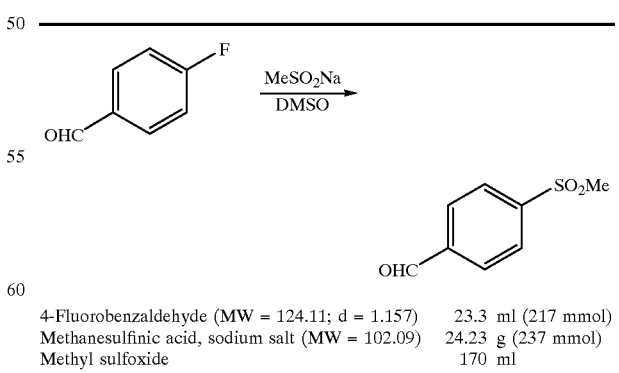

| | |
|---|---|
| 4-Fluorobenzaldehyde (MW = 124.11; d = 1.157) | 23.3 ml (217 mmol) |
| Methanesulfinic acid, sodium salt (MW = 102.09) | 24.23 g (237 mmol) |
| Methyl sulfoxide | 170 ml |

Reagents were added to methyl sulfoxide and heated to 130° C. for 18 hrs. The sodium methanesulfinate was partially insoluble at RT but went into solution at 130° C.

Sodium fluoride precipitated out of solution. The reaction mixture was poured into 300 ml water. The product precipitated out as a white solid. The reaction mixture was filtered. The product recovered was washed with 100 ml water and 2×50 ml methanol to remove methyl sulfoxide. The solvent was evaporated from the product under reduced pressure affording 39.9 g of 2 as a white powder (86% isolated yield). $C^{13}$-NMR (CDCl$_3$): 44.33, 128.25, 130.43, 139.70, 145.38, 190.72.

4-Methylsulfonylbenzaldehyde 2 from 4-Chlorobenzaldehyde

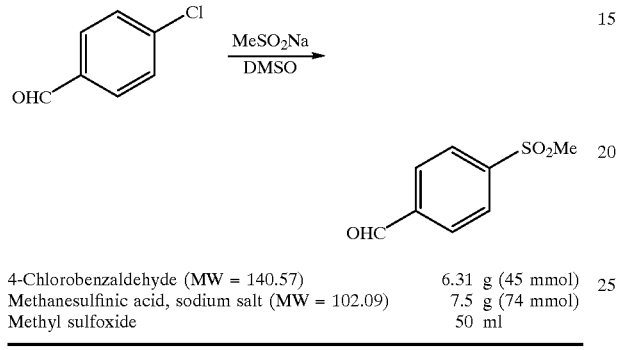

| 4-Chlorobenzaldehyde (MW = 140.57) | 6.31 g (45 mmol) |
| Methanesulfinic acid, sodium salt (MW = 102.09) | 7.5 g (74 mmol) |
| Methyl sulfoxide | 50 ml |

Reagents were added to methyl sulfoxide and heated to 130° C. for 18 hrs.

The sodium methanesulfinate was partially insoluble at RT but went into solution at 130° C. Sodium chloride precipitated out of solution. The reaction mixture was poured into 100 ml water. The product precipitated out as a white solid. The reaction mixture was filtered. The product recovered was washed with 50 ml water and 2×25 ml methanol to remove methyl sulfoxide. The solvent was evaporated from the product under reduced pressure affording 5.1 g of 4-methylsulfonyl benzaldehyde as a white powder (62% isolated yield).

Horner/Wittig Route for the Preparation of 1-(3-pyridyl)-2-(4-methylsulfonylphenyl)-ethane-1-one

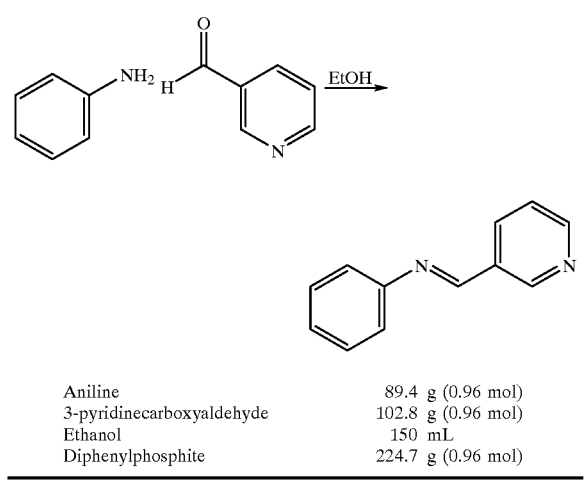

| Aniline | 89.4 g (0.96 mol) |
| 3-pyridinecarboxyaldehyde | 102.8 g (0.96 mol) |
| Ethanol | 150 mL |
| Diphenylphosphite | 224.7 g (0.96 mol) |

Ref: H. Zimmer, J. P. Bercz, Liebigs Ann. Chem. 1965, 686, 107–114.

A solution of aniline in ethanol (50 mL) was added to a solution of 3-pyridine carboxaldehyde in ethanol (100 mL) at 0° C. After 2 hours diphenylphosphite was added and stirring was continued at room temperature for 18 hours. Methyltertbutylether (400 mL) was added to further precipitate the product which was filtered, washed (MTBE) and dried under vacuum to afford 320 g (80%) of the Pyridyl-amino diphenylphosphonate as a white solid. $^{13}$-C NMR (CDCl$_3$):

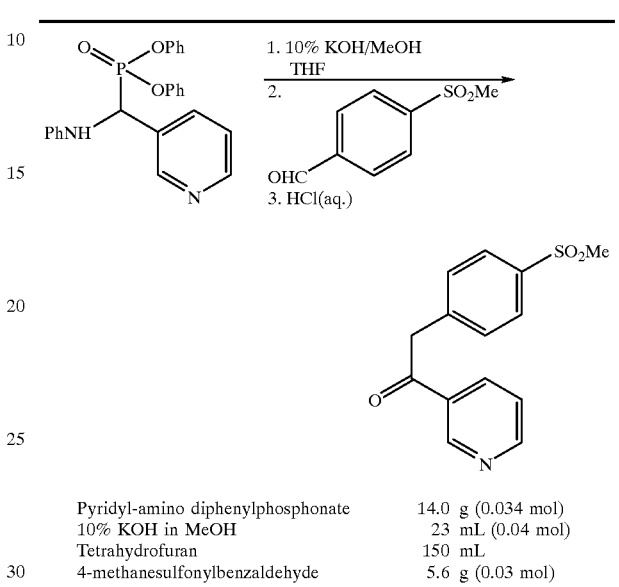

| Pyridyl-amino diphenylphosphonate | 14.0 g (0.034 mol) |
| 10% KOH in MeOH | 23 mL (0.04 mol) |
| Tetrahydrofuran | 150 mL |
| 4-methanesulfonylbenzaldehyde | 5.6 g (0.03 mol) |

10% KOH/MeOH (23 mL) was added over 10 minutes to a solution of phosphonate (14.0 g) in tetrahydrofuran at −45° C. After a further 10 minutes benzaldehyde was added in one portion and after 1 hour the reaction mixture was allowed to warm to ambient temperature. Aqueous hydrochloric acid (2N, 100 mL) was added and the solution was left standing for 18 hours. EtOAc (200 mL) and water (200 mL) were added and the organic layer discarded. The acid layer wash basified (PH=9) with sodium carbonate and extracted with dichloromethane (2×150 mL). The organic layers were combined, dried (MgSO$_4$) and concentrated. Trituration with hexanes afforded 4-methylsulfonyl benzyl-3-pyridyl ketone as a pale yellow solid (6.3 g; 76%). $^{13}$-C NMR (D-6 DMSO): 196.4, 153.6, 149.4, 140.8, 139.1, 135.7, 131.5, 130.9, 126.8, 123.9, 44.6 and 43.5 ppm.

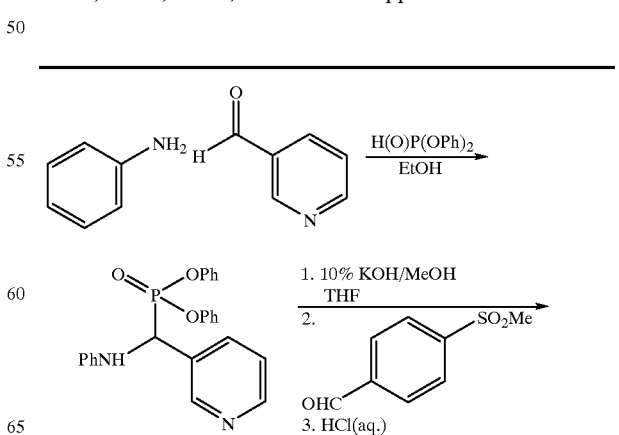

-continued

[Structure: 4-(SO2Me)-phenyl-CH2-C(=O)-3-pyridyl]

| Aniline | 4.47 g (0.05 mol) |
|---|---|
| 3-pyridinecarboxaldehyde | 5.36 g (0.05 mol) |
| Methanol | 10 mL |
| Diphenylphosphite | 11.2 g (0.05 mol) |
| 10% KOH in MeOH | 28 mL (0.05 mol) |
| 4-methanesulfonylbenzaldehyde | 8.3 g (0.45 mol) |

A solution of aniline in methanol (5 mL) was added to a solution of 3-pyridine carboxaldehyde in methanol (5 mL) at 0° C. After 2 hours diphenylphosphite was added and stirring was continued at room temperature for 18 hours. THF (100 mL) was added and the reaction ws cooled to −40° C. 10% KOH/methanol (28 mL) was added and after 30 minutes 4-methanesulfonylbenzaldehyde (8.3 g) was added. The reaction was allowed to warm to room temperature and stirred for 18 hours. EtOAc (200 mL) and water (200 mL) were added and the organic layer discarded. The acid layer wash basified (pH=9) with sodium carbonate and extracted with dichloromethane (2×150 mL). The organic layers were combined, dried (MgSO$_4$) and concentrated. Trituration with hexanes afforded 4-methylsulfonyl benzyl-3-pyridyl ketone as a pale yellow solid (9.7 g; 71%).

PREPARATION OF CHLOROMALONDIALDEHYDE

A number of routes are available for the preparation of chloromalondialdehyde.

Preparation from 1,1,2,3,3-Pentachloropropane

Cl$_2$HC-CHCl-CHCl$_2$ →(KOH, EtOH) ClHC=CCl-CHCl$_2$ →(H$_2$SO$_4$, H$_2$O) Cl-C(=CH-OH)-CHO

A detailed experimental is published in Houben-Weyl-Muller: Methoden der Organischen Chemie, 4th Edit., Vol 7/1, Thieme Verlag, Stuttgart, 1954, page 119. The starting material 1,1,2,3,3-pentachloropropane is commercially available from Pfaltz and Bauer.

Preparation from Mucochloric Acid

Cl-C(COOH)=C(Cl)-CHO →(PhNH$_2$) Cl-C(=CH-NPh)-CH=NPh ... →(H$_2$O) ...

→(NaOH) Cl-C(CHO)=CH-OH

The following is a slight variation of the original procedure of Dieckmann (Ber. Deut. Chem. Ges. 1904, 37, 4638).

Mucochloric acid 50.0 g (0.30 mol)
Aniline 54 mL (0.60 mol)
Water 1000 mL

To a solution of aniline in water at 85° C. in a vigorously stirred 2 L flask was added mucochloric acid in small portions over 30 min. On addition of the mucochloric acid, a yellow color develops, which quickly dissipated. The reaction mixture stayed heterogeneous and filtration of an aliquot after 30 min heating indicated completion of the reaction.

The reaction mixture was heated at 90° C. for 60 min., cooled to 50° C. and filtered. The filtercake was washed with 50 mL of 2N HCl and 100 mL of H$_2$O. The product was dried in a N$_2$ stream to give 57 g (100% yield) of 3-anilido-2-chloro-acrolein as a gray solid. $^{13}$C NMR (D$_6$-DMSO in ppm):108, 117, 124, 129, 140. 147, 182.

3-Anilido-2-chloro-acrolein 57 g (0.30 mol)
5N NaOH solution 120 mL (0.6 mol)

A solution of 3-anilido-2-chloro-acrolein in 120 mL of 5N NaOH was heated to 100° C. for 90 min. The dark black solution was extracted twice with 50 mL each of MTBE.

The first organic wash removed most of the dark color from the solution, and the second organic wash was only lightly colored.

On cooling the aqueous phase, a crystalline precipitate formed. This product was the 3-chloromalondialdehyde Na salt.

The aqueous phase was acidified by the addition of 60 mL of 37% HCl solution. The aqueous phase was extracted (MTBE/THF 50/50, 400 mL total) and the combined organic phases were dried over MgSO4. After treatment with Darco G60 and filtration through a plug of SiO2, the solution was evaporated to give 19.6 g (62% overall yield) of chloromalondialdehyde as a dark solid. Recrystallization from ca. 10 mL of MTBE gave 11.13 g of pure chloromalondialdehyde as a tan solid. $^{13}$C NMR (D$_6$-DMSO in ppm): 113,175 (broad).

Preparation from Chloroacetylchloride

Cl-CH$_2$-C(=O)-Cl →(DMF, (COCl)$_2$) →(H$_2$O) →(NaOH) Cl-C(CHO)=CH-ONa

Arnold (Collect. Czech. Chem. Commun. 1961, 26, 3051) mentions the formation of 3-dimethylamino-2-chloro-acrolein by reaction of chloroacetic acid with the Vilsmeyer reagent derived from POCl3 and DMF. A variation and extension of his procedure prepares chloromalondialdehyde as its Na salt.

Oxalylchloride (280 mL, 3.2 mol) was added at 10° C. to 1000 mL of DMF. The reaction was highly exothermic and a heavy precipitate formed. After a 2 h age, chloroacetylchloride (110 mL, 1.4 mol) was added and the reaction mixture was warmed to 75° C. for 3 hours. Analysis of an aliquot by $^1$H NMR indicated complete consumption of the chloroacetylchloride and the reaction mixture was quenched by addition into 1 L of H$_2$O. To the cooled solution was added 500 mL of a 50% NaOH solution. The reaction mixture is heated to reflux for 5 hours. On cooling a precipitate formed, which was filtered and washed with water. The tan solid was dried in a N$_2$ stream to give 84 g of a tan solid (54% yield).

What is claimed:

1. A compound which is

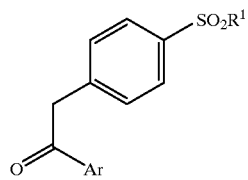

R$^1$ is selected from the group consisting of
   (a) CH$_3$,
   (b) NH$_2$,
   (c) NHC(O)CF$_3$,
   (d) NHCH$_3$; and Ar is a mono-, di-, or trisubstituted pyridinyl (or the N-oxide thereof), wherein the substituents are chosen from the group consisting of
   (a) halo,
   (b) C$_{1-4}$alkoxy,
   (c) C$_{1-4}$alkylthio,
   (d) CN,
   (e) C$_{1-4}$alkyl, and
   (f) C$_{1-4}$fluoroalkyl.

2. A compound according to claim 1 wherein R$^1$ is CH$_3$ or NH$_2$; and

Ar is a mono- or di-substituted 3-pyridinyl and the substituents are selected from the group consisting of
   (a) halo,
   (b) C$_{1-3}$alkyl,
   (c) CF$_3$, and
   (d) CN.

* * * * *